US012761194B2

(12) United States Patent
Abolins et al.

(10) Patent No.: US 12,761,194 B2
(45) Date of Patent: Oct. 13, 2026

(54) CROSS QUALITY CONTROL OF MUD LOGGING MEASUREMENTS

(71) Applicant: Schlumberger Technology Corporation, Sugar Land, TX (US)

(72) Inventors: Nicholas Abolins, Paris (FR); Pierrick Ferrando, Magny-le-Hongre (FR)

(73) Assignee: Schlumberger Technology Corporation, Sugar Land, TX (US)

(*) Notice: Subject to any disclaimer, the term of this patent is extended or adjusted under 35 U.S.C. 154(b) by 290 days.

(21) Appl. No.: 18/593,217

(22) Filed: Mar. 1, 2024

(65) Prior Publication Data

US 2025/0116640 A1 Apr. 10, 2025

(30) Foreign Application Priority Data

Oct. 5, 2023 (EP) .................................... 23306710

(51) Int. Cl.

| | |
|---|---|
| ***G01N 30/88*** | (2006.01) |
| ***E21B 21/06*** | (2006.01) |
| ***E21B 49/00*** | (2006.01) |
| ***G01N 30/02*** | (2006.01) |
| ***G01N 33/00*** | (2006.01) |
| ***G01N 33/28*** | (2006.01) |
| ***G01N 35/00*** | (2006.01) |

(52) U.S. Cl.

CPC ........... *G01N 30/88* (2013.01); *E21B 21/067* (2013.01); *E21B 49/005* (2013.01); *G01N 33/0027* (2013.01); *G01N 33/2823* (2013.01); *G01N 35/00613* (2013.01); *G01N 2030/025* (2013.01)

(58) Field of Classification Search

CPC ........... G01N 33/2823; G01N 33/0027; G01N 35/00613; G01N 30/88; E21B 21/067; E21B 49/005

See application file for complete search history.

(56) References Cited

U.S. PATENT DOCUMENTS

| | | | | | |
|---|---|---|---|---|---|
| 4,635,735 | A * | 1/1987 | Crownover | E21B 49/08 175/48 |
| 5,154,078 | A * | 10/1992 | Codazzi | E21B 49/005 175/48 |
| 6,826,482 | B2 | 11/2004 | Pandey | |
| 7,822,554 | B2 | 10/2010 | Zuo | |
| 8,838,390 | B1 * | 9/2014 | Selman | E21B 47/00 702/9 |
| 10,184,334 | B2 | 1/2019 | Betancourt-Pocaterra | |
| 10,550,692 | B2 | 2/2020 | He | |

(Continued)

FOREIGN PATENT DOCUMENTS

| | | | | |
|---|---|---|---|---|
| EP | 3020916 | A1 * | 5/2016 | G01N 33/2823 |
| SU | 1120090 | A1 * | 10/1984 | |
| WO | 2023081011 | A1 | 5/2023 | |

*Primary Examiner* — Helen C Kwok

(74) *Attorney, Agent, or Firm* — Jeffrey D. Frantz

(57) ABSTRACT

A method for mud logging includes making first gas measurements of a first gas sample obtained from circulating drilling fluid on a drill rig using a first gas chain; making second gas measurements of a second gas sample obtained from circulating drilling fluid on a drill rig using a second gas chain; defining a quality control window for the first gas measurements from the second gas measurements; and cross quality controlling the first and second gas measurements by comparing the first gas measurements with the quality control window.

20 Claims, 5 Drawing Sheets

(56) References Cited

U.S. PATENT DOCUMENTS

| | | | | |
|---|---|---|---|---|
| 11,525,822 | B2 | 12/2022 | Baecker | |
| 11,643,927 | B2 | 5/2023 | Henao | |
| 2004/0040746 | A1* | 3/2004 | Niedermayr | E21B 44/00 175/48 |
| 2007/0175633 | A1 | 8/2007 | Kosmala | |
| 2010/0089120 | A1* | 4/2010 | Hanson | E21B 49/005 73/19.09 |
| 2013/0270011 | A1* | 10/2013 | Akkurt | E21B 49/088 175/58 |
| 2013/0311096 | A1* | 11/2013 | Greer | G01N 33/2823 175/48 |
| 2013/0338926 | A1* | 12/2013 | Gzara | E21B 43/00 702/8 |
| 2015/0322783 | A1* | 11/2015 | Rowe | G01N 33/225 175/42 |
| 2016/0153955 | A1* | 6/2016 | Strapoc | G01N 33/0047 702/24 |
| 2016/0178598 | A1 | 6/2016 | Pelletier | |
| 2020/0308963 | A1* | 10/2020 | Dröge | B01D 19/0063 |
| 2021/0350052 | A1 | 11/2021 | AlQahtani | |
| 2022/0341307 | A1 | 10/2022 | Kalyanraman | |
| 2025/0109686 | A1 | 4/2025 | Fornasier | |
| 2025/0111108 | A1 | 4/2025 | Fornasier | |

* cited by examiner

CROSS QUALITY CONTROL OF MUD LOGGING MEASUREMENTS

CROSS REFERENCE TO RELATED APPLICATIONS

This application claims priority to and the benefit of European Application No. 23306710.7, filed on Oct. 5, 2023, the entirety of which is incorporated herein by reference.

BACKGROUND

When drilling a well for the production of hydrocarbons, drilling fluid is often circulated through the well for a number of purposes. For example, drilling fluid is commonly intended to provide pressure to the subterranean formation, cool and lubricate the drill bit, flush cuttings away from the drill bit and carry them to the surface, and provide hydraulic power to various downhole tools. Drilling fluids also commonly carry formation fluids and dissolved formation gasses to the surface. Such gasses may be liberated by the drill bit as it cuts the formation and may include various alkane gasses such as methane (C1), ethane (C2), propane (C3), butane (C4), pentane (C5), and the like.

The liberated gases are commonly collected and evaluated at the surface while drilling (e.g., via gas chromatography). Such gas measurements may be used to monitor the drilling operation and various safety concerns as well as to evaluate the reservoir and the potential productivity of the wellbore being drilled. During some drilling operations the liberated gases are collected and measured using two independent gas acquisition and measurement systems. While such independent systems may provide valuable insight about the drilling operation and the contents of the reservoir, there is room for further improvement.

BRIEF DESCRIPTION OF THE DRAWINGS

For a more complete understanding of the disclosed subject matter, and advantages thereof, reference is now made to the following descriptions taken in conjunction with the accompanying drawings, in which.

DETAILED DESCRIPTION

Embodiments of this disclosure include methods and systems for making and assessing drilling fluid gas composition measurements. In one example embodiment, a disclosed method includes making first gas measurements of a first gas sample obtained from circulating drilling fluid on a drill rig using a first gas chain; making second gas measurements of a second gas sample obtained from circulating drilling fluid on a drill rig using a second gas chain; defining a quality control window for the first gas measurements from the second gas measurements; and cross quality controlling the first and second gas measurements by comparing the first gas measurements with the quality control window.

Figure 1:
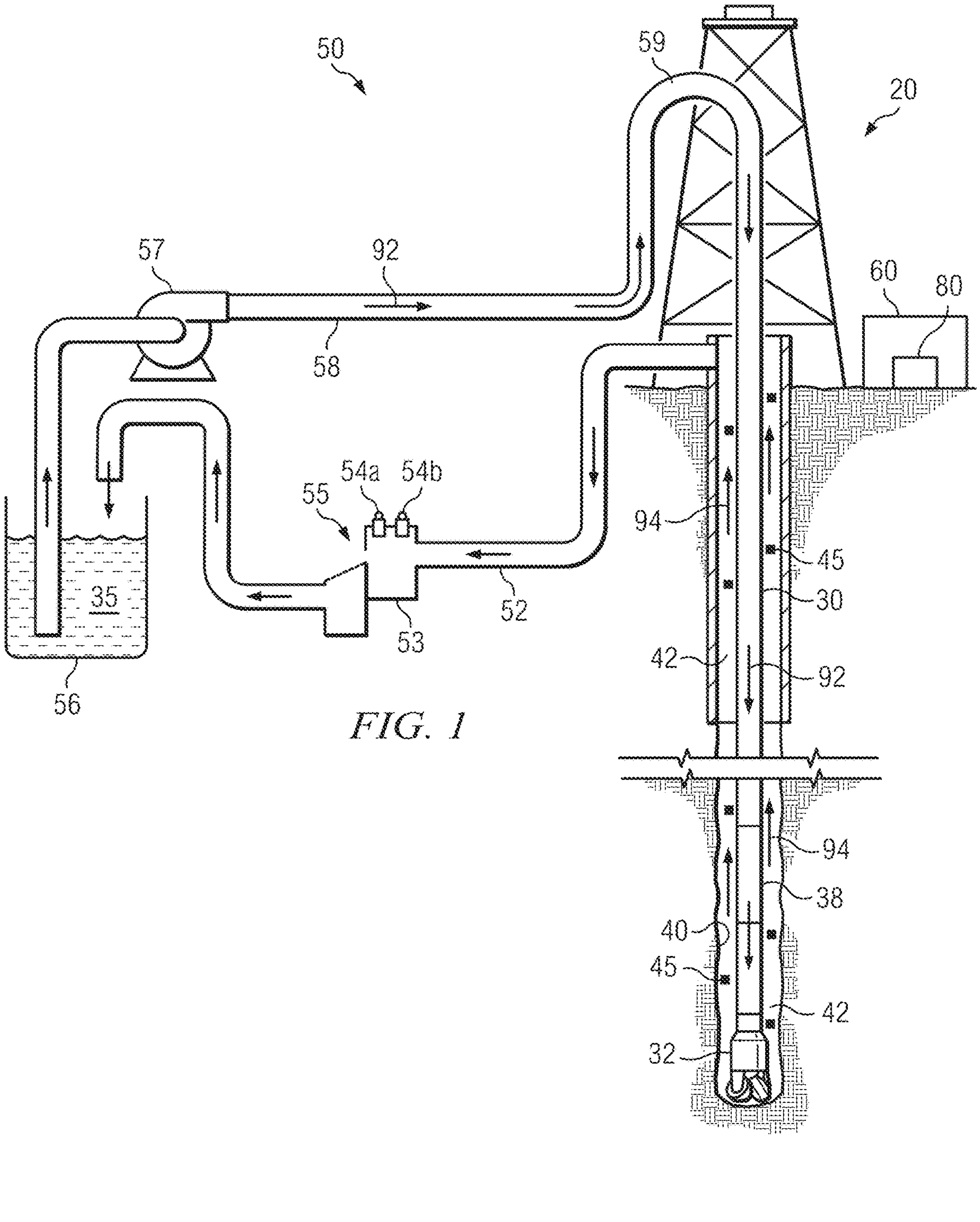
FIG. 1 depicts an example drilling rig including a disclosed system for making mud logging measurements.

FIG. 1 depicts an example drilling rig 20 including a system 80 for making mud logging measurements (e.g., for cross checking first and second parallel mud logging measurements). The drilling rig 20 may be positioned over a subterranean formation (not shown). The rig 20 may include, for example, a derrick and a hoisting apparatus (also not shown) for raising and lowering a drill string 30, which, as shown, extends into wellbore 40 and includes, for example, a drill bit 32 and one or more downhole measurement tools 38 (e.g., a logging while drilling tool or a measurement while drilling tool) in a bottom hole assembly (BHA) above the bit 32. Suitable drilling systems, for example, including drilling, steering, logging, and other downhole tools are well known in the industry.

Drilling rig 20 further includes a surface system 50 for controlling the flow of drilling fluid used on the rig (e.g., used in drilling the wellbore 40). In the example rig depicted, drilling fluid 35 may be pumped downhole (as depicted at 92), for example, via a conventional mud pump 57. The drilling fluid 35 may be pumped, for example, through a standpipe 58 and mud hose 59 in route to the drill string 30. The drilling fluid 35 typically emerges from the drill string 30 at or near the drill bit 32 and creates an upward flow 94 of mud through the wellbore annulus 42 (the annular space between the drill string and the wellbore wall). The drilling fluid 35 then flows through a return conduit 52 to a mud pit system 56 where it may be recirculated. It will be appreciated that the terms drilling fluid and mud are used synonymously herein.

The circulating drilling fluid 35 is intended to perform many functions during a drilling operation, one of which is to carrying drill cuttings 45 to the surface (in upward flow 94). The drill cuttings 45 are commonly removed from the returning mud via a shale shaker 55 (or other similar solids control equipment) in the return conduit (e.g., immediately upstream of the mud pits 56). Gases that are released or generated during drilling may also be carried to the surface in the circulating drilling fluid. These gasses, which may be dissolved in the mud or in the form of bubbles, are commonly removed from the drilling fluid, for example, via one or more degassers 54*a*, 54*b* located in or near a header tank 53 that is immediately upstream of the shale shaker 55 in the example depiction. The drill cuttings 45 and the extracted gases are commonly examined at the surface to assist the drilling operation and to evaluate the formation layers through which the wellbore is drilled.

As is known to those of ordinary skill in the art, formation gas may be released into the wellbore 40 via the drilling process (e.g., crushing the formation rock by the mechanical action of the drill bit) and may also migrate into the wellbore 40, for example, via fractures in the formation rock. The drilling process may also generate gases, for example, via drill bit metamorphism (DBM). Once in the wellbore, the gases may be transported to the surface via the drilling fluid (in the upwardly flowing fluid 94). The gases may be in solution (dissolved) in the drilling fluid and/or in the form of bubbles and may be sampled in the surface system, for example, via one or more drilling fluid degassers 54*a*, 54*b* and/or a head space gas probe. The disclosed embodiments are not necessarily limited in regards to how the gas is sampled.

With further reference to FIG. 1, drilling rig 20 may further include a testing facility 60 (e.g., a mud logging system or a laboratory trailer including one or more instruments suitable for making various measurements of sampled gases in the drilling fluid). In the depicted embodiment, the testing facility 60 has instrumentation (such as a gas chromatography apparatus) that is configured to measure the formation gas composition. The facility may further include a system 80 configured for making mud logging measurements including the disclosed quality control procedures. The system 80 may include the instrumentation or may be configured to receive the gas composition measurements from the instrumentation (e.g., the gas chromatography apparatus). The testing facility 60 may, of course, include numerous other testing instruments known to those of ordinary skill as well as computer hardware and software configured to assess the gas composition measurements and various drilling and environmental parameters. The hardware may include one or more processors (e.g., microprocessors) which may be connected to one or more data storage devices (e.g., hard drives or solid state memory) and user interfaces. It will be further understood that the disclosed embodiments may include processor executable instructions stored in the data storage device. The disclosed embodiments are, of course, not limited to the use of or the configuration of any particular computer hardware and/or software.

It will of course be appreciated that while FIG. 1 depicts a land rig 20, that the disclosed embodiments are equally well suited for land rigs or offshore rigs. As is known to those of ordinary skill, offshore rigs commonly include a platform deployed atop a riser that extends from the sea floor to the surface. The drill string extends downward from the platform, through the riser, and into the wellbore through a blowout preventer (BOP) located on the sea floor. The disclosed embodiments are expressly not limited in these regards.

Figure 2:
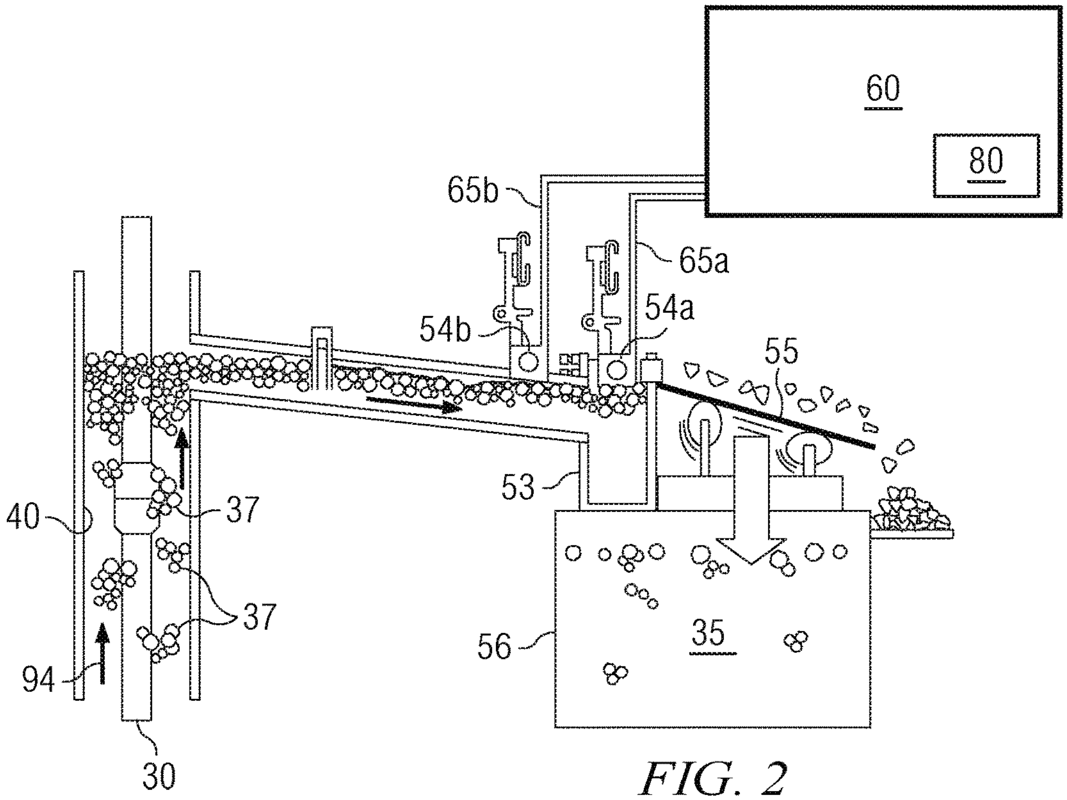
FIG. 2 depicts another embodiment of a surface system for making mud logging measurements.

FIG. 2 depicts another view of a portion of surface system 50. As described above, the return conduit 52 is configured to carry drilling fluid 35 (sometimes including gas bubbles 37) from wellbore 40 to mud pit 56. The example system 50 includes first and second degassers 54*a*, 54*b* deployed, for example, in or near a header tank 53 that is immediately upstream of the shale shaker 55 and mud pit 56. In this example configuration, the degassers 54*a*, 54*b* are configured to remove gases from the drilling fluid that emerges from the wellbore 40 (referred to in the industry as gas-out). Small volumes of the drilling fluid may be circulated through each of the degassers 54*a*, 54*b*, where they are agitated and optionally heated to remove alkane and other gases from the volumes of fluid. While the disclosed embodiments are not limited in this regard, it will be appreciated that a first degasser 54*a* may provide gases that are utilized primarily to evaluate the drilling operation and various safety concerns and a second degasser 54*b* may provide gases that are utilized for evaluating the reservoir and the potential productivity of the wellbore being drilled. In such operations, as described in more detail below, the first and second degassers 54*a*, 54*b* are coupled to corresponding first and second gas measurement devices and provide independent measurements of the wellbore gas composition.

It will be appreciated that degassers 54*a*, 54*b* may include substantially any suitable degassers, for example, including vacuum degassers, centrifugal degassers, and impeller degassers. The degassers may further be configured to heat the drilling fluid 35 to promote enhanced degassing of the fluid. The disclosed embodiments are not limited in regard to the type of degasser employed. It will further be appreciated that the first and second degassers 54*a*, 54*b* do not necessarily (and generally do not) include the same type of degasser. In other words, the first degasser 54*a* is commonly (although not always) of a different type and configuration than the second degasser 54*b*.

As further depicted in FIG. 2, in example embodiments, the degassers 54*a*, 54*b* may be piped directly to the mud logging unit or rig laboratory 60 (e.g. as depicted at 65*a*, 65*b*), for example, to automatically transport the sampled gases for compositional testing. Moreover, while not depicted, the system 50 may include one or more pumps (e.g., suction or pressure boosting pumps) configured to pump sampled gas from the degasser(s) 54*a*, 54*b* and/or the gas probe to the laboratory 60. The disclosed embodiments are, of course, not limited in regards to any sampling, pumping, or gas transport configurations.

Figure 3:
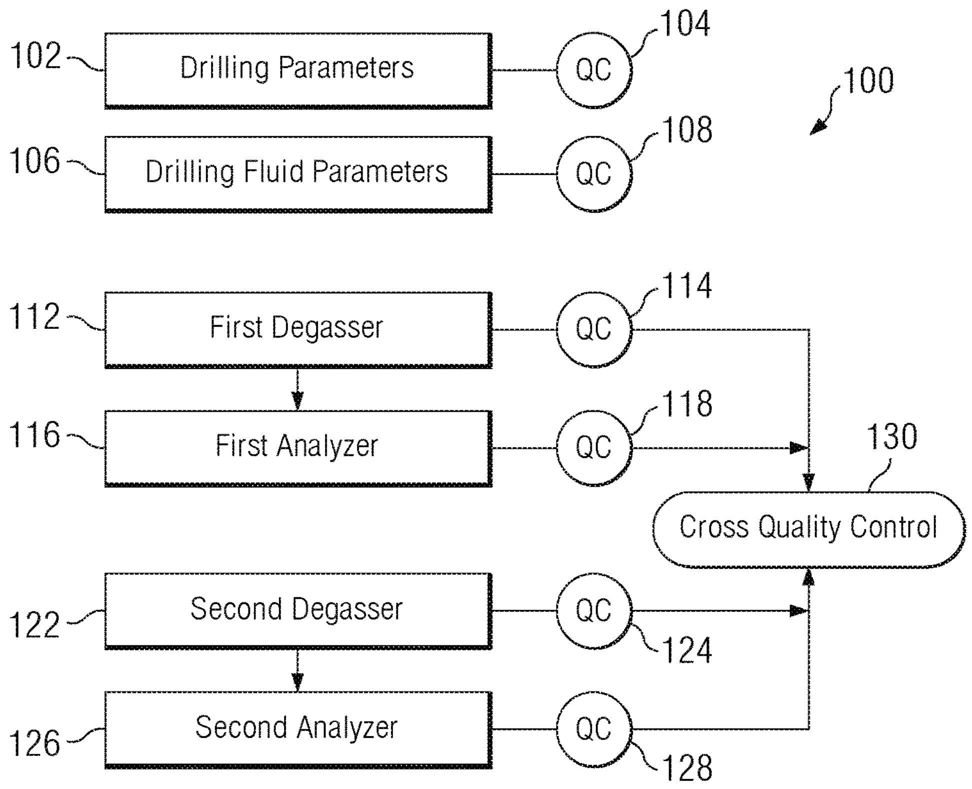
FIG. 3 depicts an example block diagram of the disclosed cross quality control.

FIG. 3 depicts an example block diagram 100 of a disclosed mud logging configuration. In the depicted embodiment, independent quality control (QC) procedures are implemented for a number of drilling and mud logging apparatuses. For example, various drilling parameters may be measured at 102. An independent QC of these measurements may be provided at 104. The drilling parameters may be measured using various rig equipment and may include, for example, a weight or load on the drill bit (WOB), a rotation rate of the drill string (RPM), a measured torque, a rate of penetration while drilling, a drilling fluid flow rate or pumping rate, and a mud pit volume or depth. QC for these drilling parameters may include checking the measured values versus predefined specification limits as well as calibrating the sensors used to make the measurements.

Various drilling fluid parameters may be measured at 106. An independent QC of these measurements may be provided at 108. The drilling fluid parameters may include various American Petroleum Institute (API) measurements such as mud density; viscosity and gel strength; oil, water, low-gravity solids and weighting material concentrations; pH and alkalinity; elemental concentrations of calcium and chloride; and electrical stability. These properties may be measured using various rig or laboratory equipment which may have independent QC procedures (e.g., at 108). As with the above parameters, QC for the drilling fluid parameters may include checking the measured values versus predefined specification limits as well as calibrating the sensors used to make the measurements.

Block diagram 100 further includes a first gas chain including a first degasser 112 and a first measurement device (an analyzer such as a GC device) 116 and a second degasser 122 and a second measurement device (an analyzer such as a GC device) 126. As noted above, each of the first and second degassers may include substantially any suitable type and configuration of degasser, for example, including vacuum degassers, centrifugal degassers, and impeller degassers, and heated degassers. The first and second analyzers 116, 126 may be configured to quantify the amounts of light alkanes and optionally other gases (e.g., alkenes and alcohols) in the gas sample. In preferred embodiments, these measurement devices quantify at least the following light alkane gases: methane (C1), ethane (C2), propane (C3), n-butane (nC4), iso-butane (iC4), n-pentane (nC5), and iso-pentane (iC5), however, the disclosed embodiments are not limited in this regard. In other embodiments, the gas measurement apparatus may quantify C1 through C8 as well as aromatics such as benzene and toluene, cyclics such as cyclopentane, methylcyclohexane and inorganics such as hydrogen, helium, carbon monoxide, and carbon dioxide.

In one example embodiment, the first gas chain may include a standard gas service, such as ReservalFlex (available from SLB), configured for monitoring the safety of the drilling operation and the second gas chain may include an advanced gas service, such as FlairFlex service (available from SLB), configured for monitoring the composition of the reservoir. The Flairflex services provides lab quality gas composition measurements of the reservoir fluids during drilling and may be used for hydrocarbon and fluid contacts identification and inter- and intra-well fluid facies mapping. It will be appreciated that the disclosed embodiments are not limited to the use of any particular gas chain configuration. Moreover, the analyzers 116, 126 may include substantially any suitable gas measurement apparatus, for example, including GC-FID, GC-TCD, GC-MS, MS, adsorption spectroscopy (e.g., IR, MID), and/or Raman spectroscopy.

The first and second gas chains may be independently quality controlled, for example, such that the first degasser 112 may be independently quality controlled at 114, the first analyzer 116 may be independently quality controlled at 118, the second degasser 122 may be independently quality controlled at 124, and the second analyzer 126 may be independently quality controlled at 128. The independent quality control procedures for the first and second degassers 112, 122 may include, for example, evaluating various degasser parameters with respect to corresponding threshold based alarms. These degasser parameters may include, for example, a flow rate of drilling fluid through the degasser, a drilling fluid level in the degasser, a drilling fluid temperature in a heated degasser, an impeller speed in an impeller degasser, and a vacuum level in a vacuum degasser. The various degasser sensors may also be calibrated from time to time to ensure accurate measurements.

The quality control procedures for the first and second analyzers 116, 126 may include evaluating various analyzer parameters with respect to corresponding threshold based alarms. These analyzer parameters may include, for example, a gas sample line pressure, an analyzer pump pressure, an analyzer exhaust flow rate, and an analyzer detector-head oven temperature. Moreover, the first and second analyzers 116, 126 may be calibrated using control samples including known amounts (or concentrations) of one or more alkane gases. The calibration may include determining peak heights and/or peak areas corresponding to individual alkane gases and further determining coefficients such that the estimated composition of the control samples is close to or equal to the known composition thereof.

With further reference to FIG. 3, the disclosed embodiments further include a cross quality control check 130 in which the first and second gas measurements are quality controlled against each other. For example, the gas composition measurements made by the first gas chain (the first degasser and first analyzer) may be quality controlled with respect to the gas composition measurements made by the second gas chain (the second degasser and second analyzer). Likewise, the gas composition measurements made by the second gas chain may also be quality controlled with respect to the gas composition measurements made by the first gas chain. In such embodiments, the cross quality control check 130 may define an expected operating window (e.g., an expected range of amounts or concentrations) for selected ones of the measured gas components in one gas chain (e.g., C1, C2, C3, iC4, nC4, iC5, or nC5) with respect to the corresponding measured gas components in the other gas chain. The disclosed cross quality control check 130 may provide an advanced warning of problems associated with either of the gas chains and may further advantageously assist operators in quickly identifying and remedying such problems.

Figure 4A:
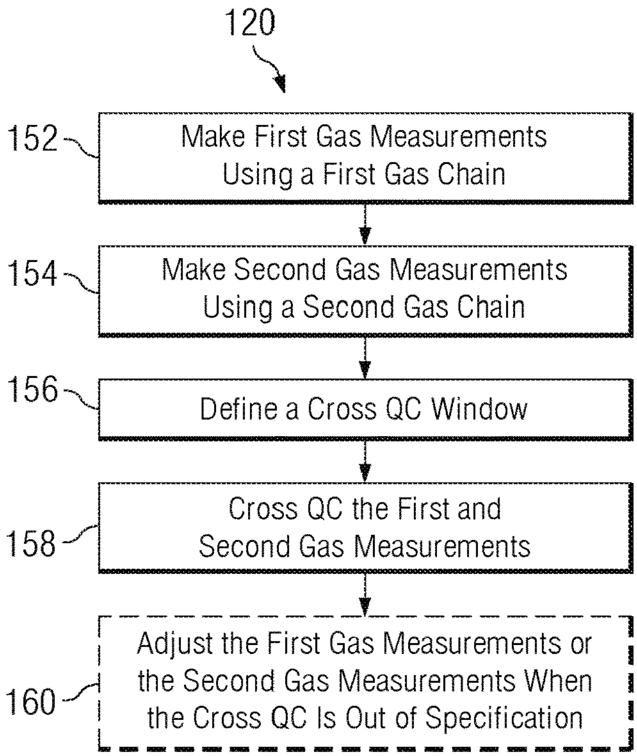
FIGS. 4A and 4B (collectively FIG. 4) depict flow charts of example mud logging methods employing the disclosed quality control methodology.
Figure 4B:
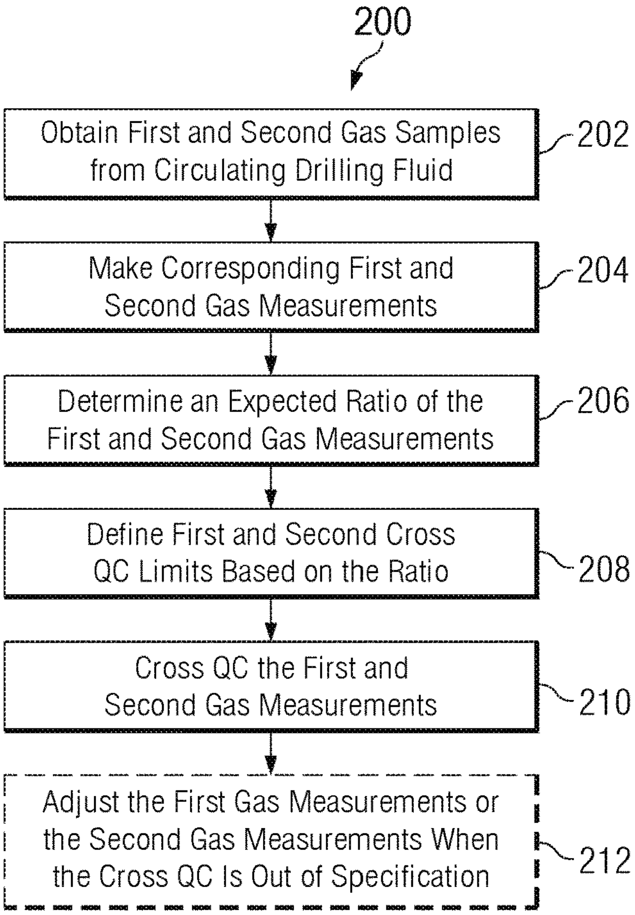

Turning now to FIGS. 4A and 4B (collectively FIG. 4) flow charts of example methods 120 and 200 for mud logging are depicted. Methods 120 and 200 may be conducted, for example, while drilling a subterranean wellbore. In FIG. 4A, first amounts of selected alkane gases in circulating drilling fluid may be measured at 152 using a first gas chain (e.g., a first degasser and a first gas analyzer) and second amounts of the selected alkane gases may be measured at 154 using a second gas chain (e.g., a second degasser and a second gas analyzer). In example embodiments, the first and second gas measurements may be made substantially simultaneously at 152, 154 while drilling a wellbore. At least one cross quality control window may be defined at 156. For example, a first cross quality control window may define an expected operating window (e.g., an expected range of amounts) for the first gas measurements made at 152 with respect to the second gas measurements made at 154. Likewise, a second cross quality control window may define an expected operating window for the second gas measurements made at 154 with respect to the first gas measurements made at 152. The first and second gas measurements may be cross quality controlled at 158, for example, by comparing the first gas measurements with the first quality control window and/or comparing the second gas measurements with the second quality control window. Method 120 may optionally further include adjusting the first gas measurements or the second gas measurements at 160 when the comparison at 158 is unfavorable. By unfavorable it is meant that the first gas measurement is not within the first quality control window and/or the second gas measurements are not within the second quality control window.

In FIG. 4B, method 200 may include obtaining first and second distinct gas samples from circulating drilling fluid used while drilling a wellbore via first and second distinct degassers at 202. Corresponding first and second gas measurements may be made at 204 on the first and second gas samples to obtain first and second amounts of selected alkane gases (and optionally other gases). An expected ratio of the first and second amounts (e.g., the first amount to the second amount or the second amount to the first amount) may be determined at 206. First and second (or upper and lower) limits may be defined at 208 based on the expected ratio determined at 206 to thereby define a cross quality control window. The first and second gas measurements may be cross quality controlled at 210, for example, by comparing the one or both of the first and second gas measurements with a corresponding quality control window (or windows). Method 200 may optionally further include adjusting a procedure utilized to obtain one or both of the first and second gas samples or a procedure used to make the first and second gas measurements at 212 when the comparison at 210 is unfavorable (e.g., when the first and second measurements are out of specification with one another).

The gas samples may be obtained and the gas measurements may be made, for example, as described above with respect to FIGS. 2 and 3 using substantially any suitable degassers and gas analyzers (measurement devices) such as a GC measurement device. The gas measurements may include amounts or volume fractions of various alkane gases such as C1, C2, C3, iC4, nC4, iC5, and nC5 as well as other common wellbore gases. Moreover, the disclosed cross quality control may be conducted for any number of the measured gases, for example, for each of the measured gases or for some selected subset of the measured gases.

With continued reference to FIG. 4, defining the cross quality control window may include determining an expected relationship between the first gas measurements and the second gas measurements, for example, an expected relationship between the first amount measured using the first gas chain and the second amount measured using the second gas chain. The expected relationship may be described, for example, as an expected ratio of the first and second amounts (e.g., the first amount to the second amount or the second amount to the first amount). In example embodiments, the ratio may be related to a ratio of the drilling fluid flow rate through the first degasser to the drilling fluid flow rate through the second degasser. This may be expressed mathematically, for example, as follows:

$$R = C \cdot \frac{F1}{F2} \tag{1}$$

where R represents the expected ratio, F1 and F2 represent calibrated or quality controlled drilling fluid flow rates through the first and second degassers, and C represents a coefficient that accounts for other factors besides drilling fluid flow rate that may impact the expected ratio. It will be appreciated that when the first and second degassers run in parallel (e.g., as depicted on FIG. 2), that the resultant gas composition measurements should have a similar trend (with time or depth) but may differ in magnitude primarily (but not exclusively) owing to the different degasser flow rates. The exact ratio may vary due to temperature, mud rheology, degasser deployment locations, and other factors that may be accounted for with the coefficient C.

In an example implementation in which the first gas chain includes a standard gas chain configured to monitor wellbore safety and the second gas chain includes an advanced gas chain configured to evaluate the reservoir contents, the drilling fluid flow rate through the first degasser may be greater than the drilling fluid flow rate through the second degasser (e.g., by a factor in a range from about 2 to 8). In such embodiments the first gas chain may be expected to measure greater quantities of the measured gases than the second gas chain. During normal operating conditions, the measured gas quantities may be related by the aforementioned ratio, for example, as follows: M1=R·M2, where M1 and M2 represent the first and second gas measurements.

First and second (or upper and lower) cross quality control limits may be defined at 208, above and below the expected ratio, for example, as follows:

$$L1 = R + \Delta \qquad L2 = R - \Delta \tag{2}$$

where L1 and L2 represent the first and second cross quality control limits and 2Δ defines a quality control window width (such that the ratio defines the center of the control window). The first and second gas measurements may be cross quality controlled at 210, for example, by comparing the one or both of the first and second gas measurements with a corresponding quality control window (or windows). This may be expressed mathematically, for example, as follows:

$$(R - \Delta) \cdot M2 < M1 < (R + \Delta) \cdot M2 \qquad \frac{M1}{(R + \Delta)} < M2 < \frac{M1}{(R - \Delta)} \tag{3}$$

Note that to obtain an upper limit or window value for the first gas measurement M1 the second gas measurement M2 may be multiplied by a first coefficient (R+Δ) and to obtain a lower limit or window value for the first gas measurement, the second gas measurement may be multiplied by a second coefficient (R−Δ). Likewise, to obtain an upper limit or window value for the second gas measurement M2 the first gas measurement M1 may be divided by the second coefficient (R−Δ) and to obtain a lower limit or window value for the second gas measurement, the first gas measurement may be divided by the first coefficient (R+Δ).

The disclosed embodiments are now described by way of the following non-limiting hypothetical example. In this particular example, the first and second gas chains may include a standard gas service, such as ReservalFlex (available from SLB), that may be configured for monitoring the safety of the drilling operation and advanced gas service, such as FlairFlex service (available from SLB), configured for monitoring the reservoir contents. The degasser in the standard configuration may pump the drilling fluid at a flow rate of about 1500 mL per minute, whereas the degasser in the advanced configuration may pump the drilling fluid at a flow rate of about 300 mL per minute. From Eq. (1) above a ratio R=1500/300=5 may be computed (e.g., when the coefficient C is approximately 1). First and second limits may be computed from Eq. (2). For example, when Δ=1 the limits may equal 6 and 4. The standard gas measurements and advanced gas measurements may then be cross quality controlled using Eq. (3) to ensure that the following conditions apply:

$$4 \cdot AG < SG < 6 \cdot AG \qquad \frac{SG}{6} < AG < \frac{SG}{4}$$

where SG represents the measurements made using the standard gas service (the first gas measurements) and AG represents the measurements made using the advanced gas service (the second gas measurements).

Figure 5A:
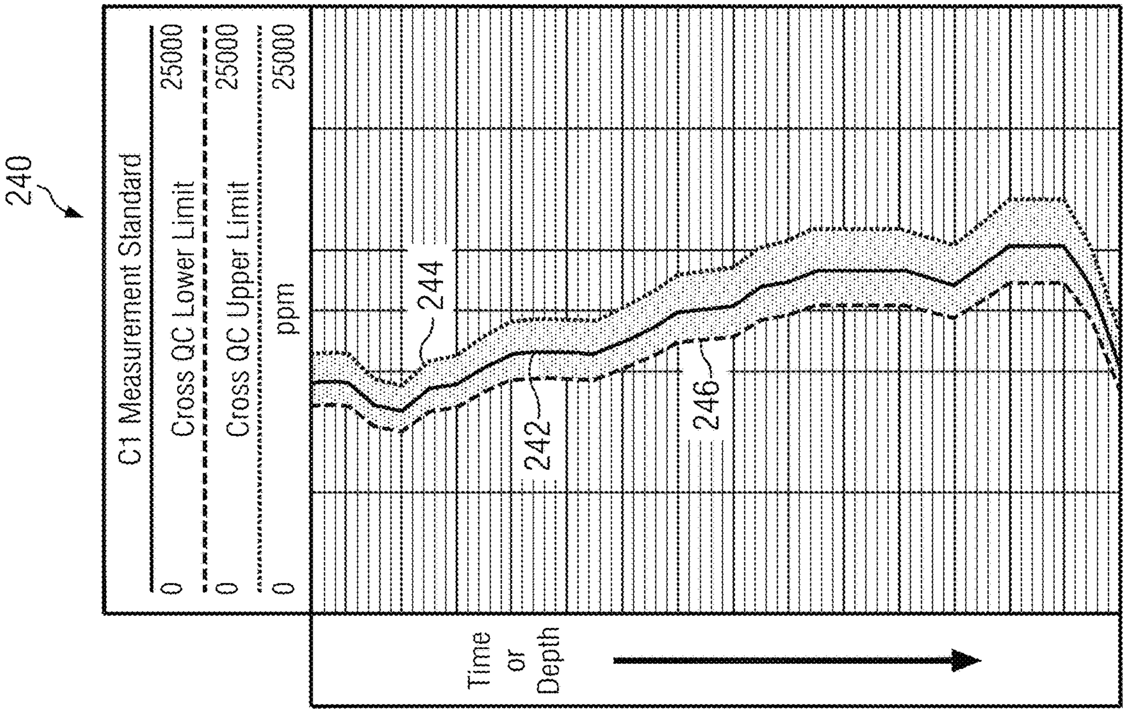
FIGS. 5A and 5B (collectively FIG. 5) depict example mud logs generated using the method disclosed in FIG. 4.
Figure 5B:
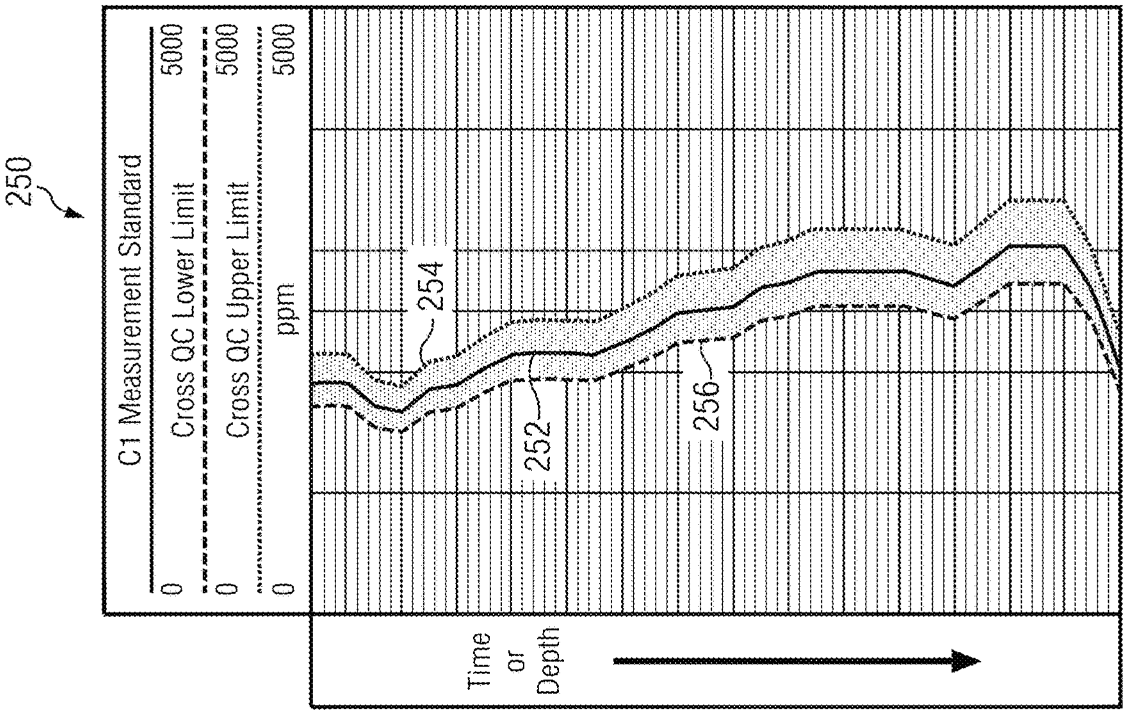

FIGS. 5A and 5B (collectively FIG. 5) depict example logs 240 and 250 illustrating the disclosed embodiments. In these figures, the first and second gas measurements of the example described above are plotted (e.g. in parts per million of methane-C1) on the horizontal axis versus time or depth on the vertical axis. FIG. 5A logs the standard gas measurement SG at 242 as well as the upper and lower cross quality control limits at the 244 and 246. In this example, the upper cross quality control limit equals six times the advanced gas measurement and the lower cross quality control limit equals four times the advanced gas limit. FIG. 5B logs the advanced gas measurement AG at 252 as well as the upper and lower cross quality control limits at the 254 and 256. In this example, the upper cross quality control limit equals one fourth the standard gas measurement and the lower cross quality control limit equals one sixth the standard gas limit. Note that in this example each of the gas measurements remains within the cross quality control specifications of the other.

Figure 6:
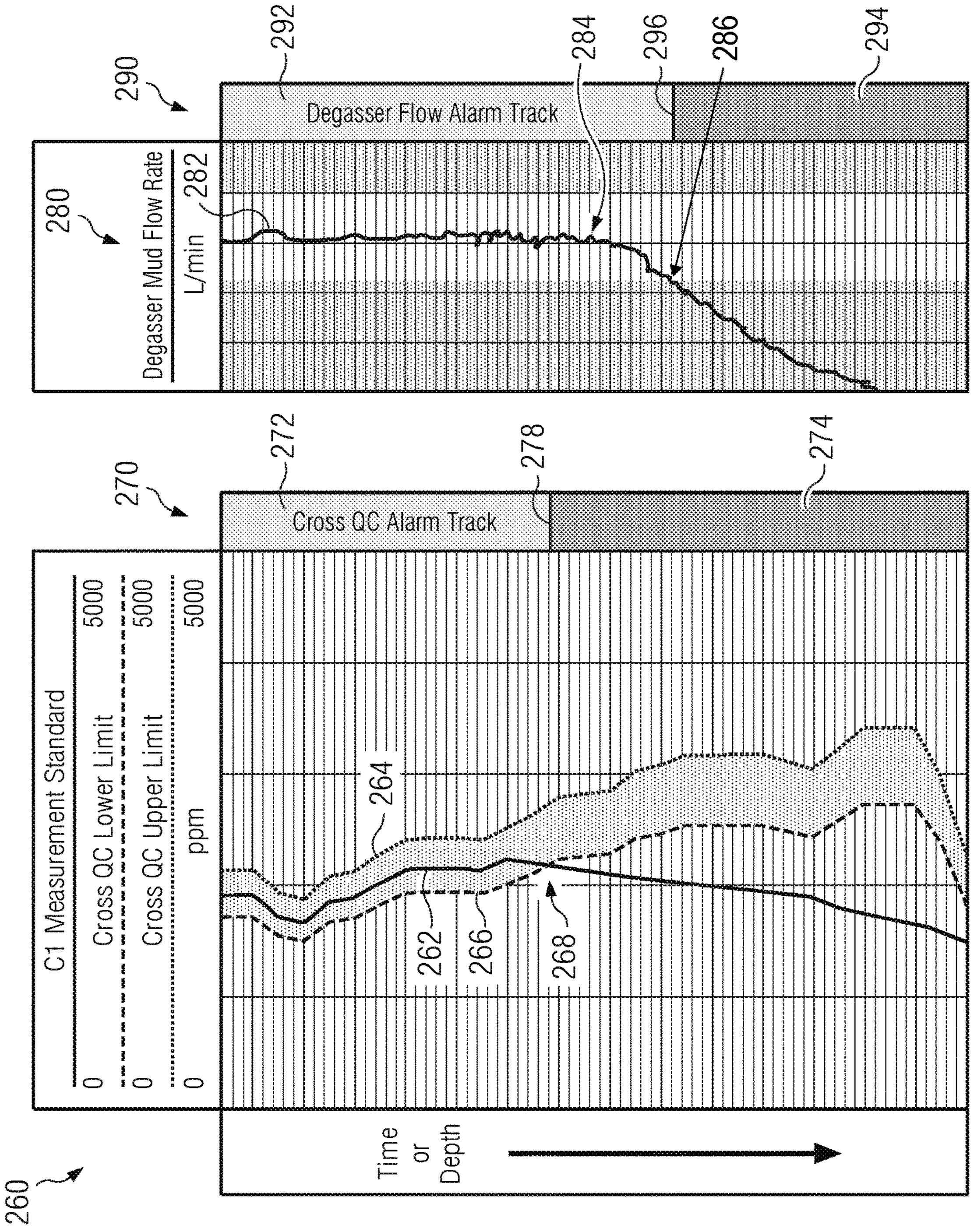
FIG. 6 depicts an example mud log further illustrating the disclosed embodiments and certain advantages thereof.

FIG. 6 depicts an example log 260 further illustrating the disclosed embodiments and certain advantages thereof. The depicted log 260 is similar to the log depicted on FIG. 5B in that it logs an advanced gas measurement AG at 262 as well as the previously described upper and lower cross quality control limits at the 264 and 266. FIG. 6 further includes a cross quality control alarm track 270 that indicates when the advanced gas measurements are within the cross quality control specifications (shown as light grey at 272) and out of the cross quality control specifications (shown as dark grey at 274). It will of course be understood that the cross quality control alarm track may provide a colored indication, for example, green when the measurements are within the cross quality control specification and red when the measurements are outside of the cross quality control specification. FIG. 6 still further includes a log 280 of the advanced gas degasser mud flow rate at 282 and a corresponding degasser flow alarm track at 290, with light gray indicating that the degasser mud flow rate is within specification at 292 and dark gray indicating that the flow rate is out of specification at 294 (of course, the alarm track may also use green and red colors to indicate in and out of specification flowrates).

In the depicted example the advanced gas measurements and the advanced gas degasser mud flow rate are both within specification early in the operation as indicated in the alarm tracks at 272 and 292. As the mud logging operation progresses, the advanced gas measurements are observed to fall below the lower cross quality control limit at 268 and thereby trigger a change in the alarm track as indicated at 278. At a similar time or depth, the degasser mud flow log indicates a change in flow rate behavior beginning at 284, however, this change in flow behavior does not yet trigger the flow rate alarm. The alarm is not triggered until a later time or depth when the degasser flow rate falls below the threshold at 286 and thereby triggers the flow rate alarm as indicated at 296. In this example, the fixed threshold degasser flow alarm 290 is not triggered until after the cross quality control alarm 270 is triggered. It can be seen that the cross quality control and the corresponding alarm may provide an advanced warning of a system error (such as degasser fouling in this example) and may therefore provide for more timely troubleshooting.

It will be understood that the present disclosure includes numerous embodiments. These embodiments include, but are not limited to, the following embodiments.

In a first embodiment, a method for mud logging comprising includes making first gas measurements of a first gas sample obtained from circulating drilling fluid on a drill rig using a first gas chain; making second gas measurements of a second gas sample obtained from circulating drilling fluid on a drill rig using a second gas chain; defining a quality control window for the first gas measurements from the second gas measurements; and cross quality controlling the first and second gas measurements by comparing the first gas measurements with the quality control window.

A second embodiment may include the first embodiment, wherein the making the first gas measurements and the making second gas measurements comprises measuring a composition of at least one alkane gas using a gas chromatography apparatus.

A third embodiment may include any one of the first through second embodiments, wherein the first gas chain comprises a first degasser and a first gas measurement device and the second gas chain comprises a second degasser and a second composition measurement device.

A fourth embodiment may include any one of the first through third embodiments, further comprising adjusting the first gas measurement or the second gas measurement when the first gas measurement is outside of the quality control window.

A fifth embodiment may include any one of the first through fourth embodiments, wherein: the making the first gas measurements comprises obtaining a first gas sample from the circulating drilling fluid using a first degasser and making the first gas measurements on the obtained first gas sample; and the making the second gas measurements comprises obtaining a second gas sample from the circulating drilling fluid using a second degasser and making the second gas measurements on the obtained second gas sample.

A sixth embodiment may include any one of the first through fifth embodiments, wherein: the first gas measurements are independently quality controlled; the second gas measurements are independently quality controlled; the defining comprises defining the quality control window for the first independently quality controlled gas measurements from the second independently quality controlled gas measurements; and the cross quality controlling comprises comparing the first independently quality controlled gas measurements with the quality control window.

A seventh embodiment may include any one of the first through sixth embodiments, wherein the defining the quality control window comprises determining an expected ratio of the first gas measurement and the second gas measurement.

An eighth embodiment may include the seventh embodiment, wherein the expected ratio is equal to a coefficient multiplied by a ratio of a drilling fluid flow rate through a first degasser used to obtain the first sample and a drilling fluid flow rate through a second degasser used to obtain the second sample.

A ninth embodiment may include any one of the seventh through eighth embodiments, wherein the defining the quality control window further comprises defining first and second control limits from the expected ratio to define the quality control window.

A tenth embodiment may include the ninth embodiment, wherein the expected ratio defines a center of the quality control window.

In an eleventh embodiment, a system for mud logging comprises a first degasser configured to obtain a first gas sample from circulating drilling fluid; a second degasser configured to obtain a second gas sample from the circulating drilling fluid; a first gas measurement device configured to make a first gas measurement of a composition of the first gas sample; a second gas measurement device configured to make a second gas measurement of a composition of the second gas sample; and a processor configured to: receive the first gas measurement and the second gas measurement; define a quality control window for the first gas measurements from the second gas measurements; and cross quality control the first and second gas measurements by comparing the first gas measurements with the quality control window.

A twelfth embodiment may include the eleventh embodiment, wherein the first gas measurement device comprises a first gas chromatography apparatus configured to measure a composition of at least one alkane gas in the first gas sample and the second gas measurement device comprises a second gas chromatography apparatus configured to measure a composition of the at least one alkane gas in the second gas sample.

A thirteenth embodiment may include any one of the eleventh through twelfth embodiments, wherein the processor is further configured to generate a log depicting the first gas measurements and the quality control window.

A fourteenth embodiment may include any one of the eleventh through thirteenth embodiments, wherein the define the quality control window further comprises determining an expected ratio of the first gas measurement and the second gas measurement, wherein the expected ratio is equal to a coefficient multiplied by a ratio of a drilling fluid flow rate through the first degasser and a drilling fluid flow rate through the second degasser.

A fifteenth embodiment may include any one of the eleventh through fourteenth embodiments, wherein the define the quality control window further comprises defining first and second control limits from the expected ratio to define the quality control window.

In a sixteenth embodiment, a method for mud logging comprises obtaining first and second gas samples from circulating drilling fluid using corresponding first and second independent degassers while drilling a subterranean wellbore; making first and second gas measurements of the corresponding first and second obtained gas samples using first and second independent gas analyzers; determining an expected ratio of the first and second gas measurements; determining first and second cross quality control limits based on the expected ratio to define a quality control window; and cross quality controlling the first and second gas measurements by comparing the first gas measurements with the quality control window.

A seventeenth embodiment may include the sixteenth embodiment, further comprising adjusting the first gas measurement or the second gas measurement when the first gas measurement is outside of the quality control window.

An eighteenth embodiment may include any one of the sixteenth through seventeenth embodiments, wherein: the first and second degassers are independently quality controlled; the first and second gas analyzers are independently quality controlled; the first and second gas measurements are independently quality controlled; the second gas measurements are independently quality controlled; and the cross quality controlling comprises comparing the first independently quality controlled gas measurements with the quality control window.

A nineteenth embodiment may include any one of the sixteenth through eighteenth embodiments, wherein the expected ratio is equal to a coefficient multiplied by a ratio of a drilling fluid flow rate through the first degasser and a drilling fluid flow rate through the second degasser.

A twentieth embodiment may include any one of the sixteenth through nineteenth embodiments, wherein the expected ratio defines a center of the quality control window.

Although cross quality control of mud logging measurements has been described in detail, it should be understood that various changes, substitutions and alterations can be made herein without departing from the spirit and scope of the disclosure as defined by the appended claims.

What is claimed is:

1. A method for mud logging comprising:

making first gas measurements of a first gas sample obtained from a circulating drilling fluid flowing through a fluid conduit on a drill rig using a first gas chain comprising a first degasser disposed at the fluid conduit extending between a wellbore and a mud pit;

simultaneous to the making the first gas measurements of the first gas sample, making second gas measurements of a second gas sample obtained from the circulating drilling fluid on the drill rig using a second gas chain comprising a second degasser disposed at the fluid conduit between the wellbore and the mud pit;

defining a quality control window for the first gas measurements from the second gas measurements; and cross quality controlling the first gas measurements and the second gas measurements by comparing the first gas measurements with the quality control window.

2. The method of claim 1, wherein the making the first gas measurements and the making the second gas measurements comprises measuring a composition of at least one alkane gas using a gas chromatography apparatus.

3. The method of claim 1, wherein the first gas chain comprises the first degasser and a first gas composition measurement device and the second gas chain comprises the second degasser and a second gas composition measurement device.

4. The method of claim 1, further comprising adjusting the first gas measurements or the second gas measurements in response to the first gas measurements being outside of the quality control window.

5. The method of claim 1, wherein:

the making the first gas measurements comprises obtaining the first gas sample from the circulating drilling fluid using the first degasser and making the first gas measurements on the first gas sample; and the making the second gas measurements comprises obtaining the second gas sample from the circulating drilling fluid using the second degasser and making the second gas measurements on the obtained second gas sample.

6. The method of claim 1, wherein:

the first gas measurements are independently quality controlled;

the second gas measurements are independently quality controlled;

the defining the quality control window comprises defining the quality control window for the first independently quality controlled gas measurements from the second independently quality controlled gas measurements; and the cross quality controlling comprises comparing the first independently quality controlled gas measurements with the quality control window.

7. The method of claim 1, wherein the defining the quality control window comprises determining an expected ratio of the first gas measurements and the second gas measurements.

8. The method of claim 7, wherein the expected ratio is equal to a coefficient multiplied by a ratio of a first drilling fluid flow rate through the first degasser used to obtain the first gas sample and a second drilling fluid flow rate through the second degasser used to obtain the second gas sample.

9. The method of claim 7, wherein the defining the quality control window further comprises defining first control limits and second control limits from the expected ratio to define the quality control window.

10. A system for assessing downhole gas composition measurements, the system comprising:

a first degasser configured to obtain a first gas sample from a circulating drilling fluid flowing through a fluid conduit extending between a wellbore and a mud pit;

a second degasser disposed at the fluid conduit between the wellbore and the mud pit, the second degasser configured to obtain a second gas sample from the circulating drilling fluid;

a first gas measurement device configured to make a first gas measurement of a composition of the first gas sample;

a second gas measurement device configured to make a second gas measurement of a composition of the second gas sample; and a processor configured to:

receive the first gas measurement and the second gas measurement;

define a quality control window for the first gas measurement from the second gas measurement; and cross quality control the first gas measurement and the second gas measurement by comparing the first gas measurement with the quality control window.

11. The system of claim 10, wherein;

the first gas measurement device comprises a first gas chromatography apparatus configured to measure a first composition of at least one alkane gas in the first gas sample; and the second gas measurement device comprises a second gas chromatography apparatus configured to measure a second composition of the at least one alkane gas in the second gas sample.

12. The system of claim 10, wherein the define the quality control window further comprises determining an expected ratio of the first gas measurement and the second gas measurement, wherein the expected ratio is equal to a coefficient multiplied by a ratio of a first drilling fluid flow rate through the first degasser and a second drilling fluid flow rate through the second degasser.

13. The system of claim 12, wherein the define the quality control window further comprises defining first control limits and second control limits from the expected ratio to define the quality control window.

14. A method for mud logging comprising:

obtaining a first gas sample from a circulating drilling fluid flowing through a fluid conduit using a first degasser and a second gas sample from the circulating drilling fluid flowing through the fluid conduit using a second degasser independent of the first degasser while drilling a subterranean wellbore, wherein:

the first degasser is disposed on the fluid conduit extending between a wellbore and a mud pit; and the first degasser comprises a first type of degasser including a vacuum degasser and the second degasser comprises a second type of degasser different than the first type of degasser, the second type of degasser including at least one of a centrifugal degasser or an impeller degasser;

making a first gas measurement corresponding to the first gas sample using a first gas analyzer and a second gas measurement corresponding to the second gas sample using a second gas analyzer independent of the first gas analyzer;

determining an expected ratio of the first gas measurement and the second gas measurement;

determining first cross quality control limits and second cross quality control limits based on the expected ratio to define a quality control window; and cross quality controlling the first gas measurement and the second gas measurement by comparing the first gas measurement with the quality control window.

15. The method of claim 14, further comprising adjusting the first gas measurement or the second gas measurement in response to the first gas measurement being outside of the quality control window.

16. The method of claim 14, wherein:

the first degasser and the second degasser are independently quality controlled;

the first gas analyzer and the second gas analyzer are independently quality controlled;

the first gas measurement and the second gas measurement are independently quality controlled;

the second gas measurement is independently quality controlled; and the cross quality controlling comprises comparing the first independently quality controlled gas measurement with the quality control window.

17. The method of claim 14, wherein the expected ratio is equal to a coefficient multiplied by a ratio of a first drilling fluid flow rate through the first degasser and a second drilling fluid flow rate through the second degasser.

18. The method of claim 14, wherein the expected ratio defines a center of the quality control window.

19. The method of claim 1, wherein the first degasser comprises a first type of degasser and the second degasser comprises a second type of degasser different than the first type of degasser.

20. The method of claim 19, wherein:

the first type of degasser comprises a vacuum degasser; and the second type of degasser comprises at least one of a centrifugal degasser or an impeller degasser.

* * * * *